(12) United States Patent
Murray, Jr. et al.

(10) Patent No.: US 6,327,334 B1
(45) Date of Patent: Dec. 4, 2001

(54) METHOD OF RAPIDLY SCREENING X-RAY POWDER DIFFRACTION PATTERNS

(75) Inventors: Richard C. Murray, Jr., Palatine; Cheryl M. Bratu, Park Ridge; Gregory J. Lewis, Mount Prospect, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/444,352

(22) Filed: Nov. 18, 1999

(51) Int. Cl.$^7$ .................................................. G01N 23/20
(52) U.S. Cl. ................................. 378/75; 378/71
(58) Field of Search .................... 378/71, 73, 75

(56) References Cited

U.S. PATENT DOCUMENTS

| | | | |
|---|---|---|---|
| 5,481,476 | * | 1/1996 | Windig ................................. 364/498 |
| 5,862,060 | | 1/1999 | Murray, Jr. ...................... 364/528.01 |

OTHER PUBLICATIONS

Minami, Y.; Miyazawa, T.; Nakajima, K.; Hida, H.; X–sen Bunseki no Shinpo, 27 (1996) 107–115. (Abstract Only).
Mitsui, T.; Okuyama, S.; Fujimura, Y. *Analytical Sciences,* 7 (1991) 941–945.
Harju, M. E.; Minkkinen, P.; Valkonen, J.; *Chemometrics and Intelligent Laboratory Systems,* 23 (1994) 341–350.

* cited by examiner

*Primary Examiner*—Craig E. Church
(74) *Attorney, Agent, or Firm*—John G. Tolomei; Frank S. Molinaro; Maryann Maas

(57) ABSTRACT

A method for rapidly screening multiple X-ray powder diffraction patterns, such as those generated through combinatorial chemistry, has been developed. The method is directed toward measuring X-ray powder diffraction patterns of a set of samples, factoring the patterns using a suitable statistical technique into a small number of discrete components or factors, determining the scores corresponding to the factors for each X-ray powder diffraction pattern, and plotting the scores. The graphs of the scores are then inspected for clusters, trends, or outliers, which may represent new material or, perhaps, faulty data.

22 Claims, 19 Drawing Sheets

METHOD OF RAPIDLY SCREENING X-RAY POWDER DIFFRACTION PATTERNS

FIELD OF THE INVENTION

This invention relates to rapidly screening multiple X-ray powder diffraction patterns, such as those generated through combinatorial chemistry. More particularly, the invention is directed toward measuring X-ray powder diffraction patterns of a set of samples, factoring the patterns using a suitable statistical technique into a small number of discrete components or factors, determining the scores corresponding to the factors for each X-ray powder diffraction pattern, and plotting the scores. The graphs of the scores are then inspected for clusters of similar materials, outliers, and trends representing transitions between material forms.

BACKGROUND OF THE INVENTION

Combinatorial chemistry is being increasingly used in the formation of new compounds. Numerous different compounds may be formed simultaneously, and what used to take days, or weeks, may now be accomplished in minutes or hours. Along with the rapid synthesis of new compounds, however, comes the task of identifying the large volume of newly synthesized compounds. For many years now, the X-ray powder diffraction analytical technique has been a favorite among chemists for identifying the structure of new compounds. However, the overall identification process may be time consuming, with each X-ray powder diffraction pattern being compared to a large number of known patterns in a library. Pattern recognition or "search and match" computer programs such as Jade 5.0, available from Materials Data Inc., have helped to more efficiently compare an unknown sample X-ray diffraction pattern to those in a library of known patterns, but the sheer volume of X-ray diffraction patterns being generated in a combinatorial chemistry application is likely to overwhelm the standard historical procedure.

This application focuses on more efficiently managing a large number of X-ray powder diffraction patterns through the use of the statistical tool of principal component analysis. Using principal component analysis allows for each X-ray powder diffraction pattern to be reduced to a set of scores which can be plotted on a 2- or more dimensional plot. A great deal of information is readily apparent to a chemist versed in the analysis of X-ray powder diffraction through inspection of the resulting plot. For example, X-ray powder diffraction patterns that are highly likely to correspond to the same compound or structure can be identified by the proximity of their scores in a cluster, thereby reducing the overall number of X-ray powder diffraction patterns that must be interpreted by comparison to libraries of known X-ray powder diffraction patterns using, for example, search and match-type software programs. Inspection of the scores plot may also indicate outliers corresponding to X-ray powder diffraction patterns that exhibit unusual characteristics as compared to the overall set of samples. A chemist may then focus attention on the X-ray powder diffraction patterns most likely to be a desired new compound without spending resources on samples represented by clusters of scores that are likely to be multiple samples of the same structure. The plot may thus reveal that of the multiple X-ray powder diffraction patterns, only a few should be investigated further. The time and labor savings to a chemist may be enormous.

Principal component analysis has been applied to other analytical data such as near infrared spectroscopy; see U.S. Pat. No. 5,862,060, for process control applications. Principal component analysis has also been used to determine the concentration of controlled substances such as heroin and cocaine when present in a mixture with other known compounds; see, Minami, Y.; Miyazawa, T.; Nakajima, K.; Hida, H.; X-sen *Bunseki no Shinpo*, 27 (1996) 107–115, and Mitsui, T.; Okuyama, S.; Fujimura, Y. *Analytical Sciences*, 7 (1991) 941–945. Haju, M. E.; Minkkinen, P.; Valkonen, J.; *Chemometrics and intelligent Laboratory Systems*, 23 (1994) 341–350 disclosed explaining and predicting ammonium nitrate solid phase transition paths between IV, III, and 11 on the basis of X-ray powder diffraction patterns and differential scanning calorimetry data by applying partial least squares regression and principal component analysis. The present invention, however, uses principal component analysis in conjunction with multiple X-ray powder diffraction patterns to gain a great amount of information on potentially widely varied samples. That is to say, the present invention is intended to be a; discovery method applied to a very large number of samples where any number of known and unknown materials may be present within the sample set. It therefore differs from the prior art which was limited to the case where all the materials present in the sample set were known a priori, and, moreover, the number of possible materials present was very limited.

SUMMARY OF THE INVENTION

The goal of the invention is to provide a method of rapidly screening multiple X-ray powder diffraction patterns. This is accomplished by reducing the large number, sometimes greater than one thousand, of angle-intensity data pairs present in each X-ray powder diffraction pattern down to a few, typically two to five, numbers called scores, which are representative of the pattern and which can be easily plotted and visualized for screening purposes. The invention involves first obtaining an X-ray powder diffraction pattern of each member in a set of samples. Principal Component Analysis (PCA) is then used to derive a number of factors representative of this data set. In conjunction with these factors, PCA simultaneously generates a corresponding set of scores assigned to each sample with each score corresponding to one of the derived factors, and together representing each pattern in the sample set. The scores of each factor are determined for each X-ray powder diffraction pattern of the sample set, and the scores are plotted in 2- or more dimensional space. The resulting plot may be visually inspected or statistically analyzed to identify clusters, trends, or outliers, which may represent new material, or possibly faulty data.

In a more specific embodiment of the invention, a subset of samples and the corresponding X-ray powder diffraction patterns may be selected. It is preferred that the subset of samples form a cluster in the first plot described above. Such clustering may be identified visually or by using various statistical techniques to define the clusters. Again, a number of factors are determined by principal component analysis which can be used in combination with scores of the factors to express each X-ray powder diffraction pattern in the subset of samples. The scores of each factor are again determined for each X-ray powder diffraction pattern of the subset of samples, and the scores are plotted in 2- or more dimensional space. As before, the resulting plot may be visually inspected or statistically analyzed to identify clusters, trends, or outliers. The overall method may be repeated where each iteration uses a selected number of the previous subset, thus using progressively smaller subsets, until the resulting plots show random scatter or there is another reason such as chemical knowledge of the sample set, to stop generating sub-clusters.

DETAILED DESCRIPTION OF THE INVENTION

Figure 1A:
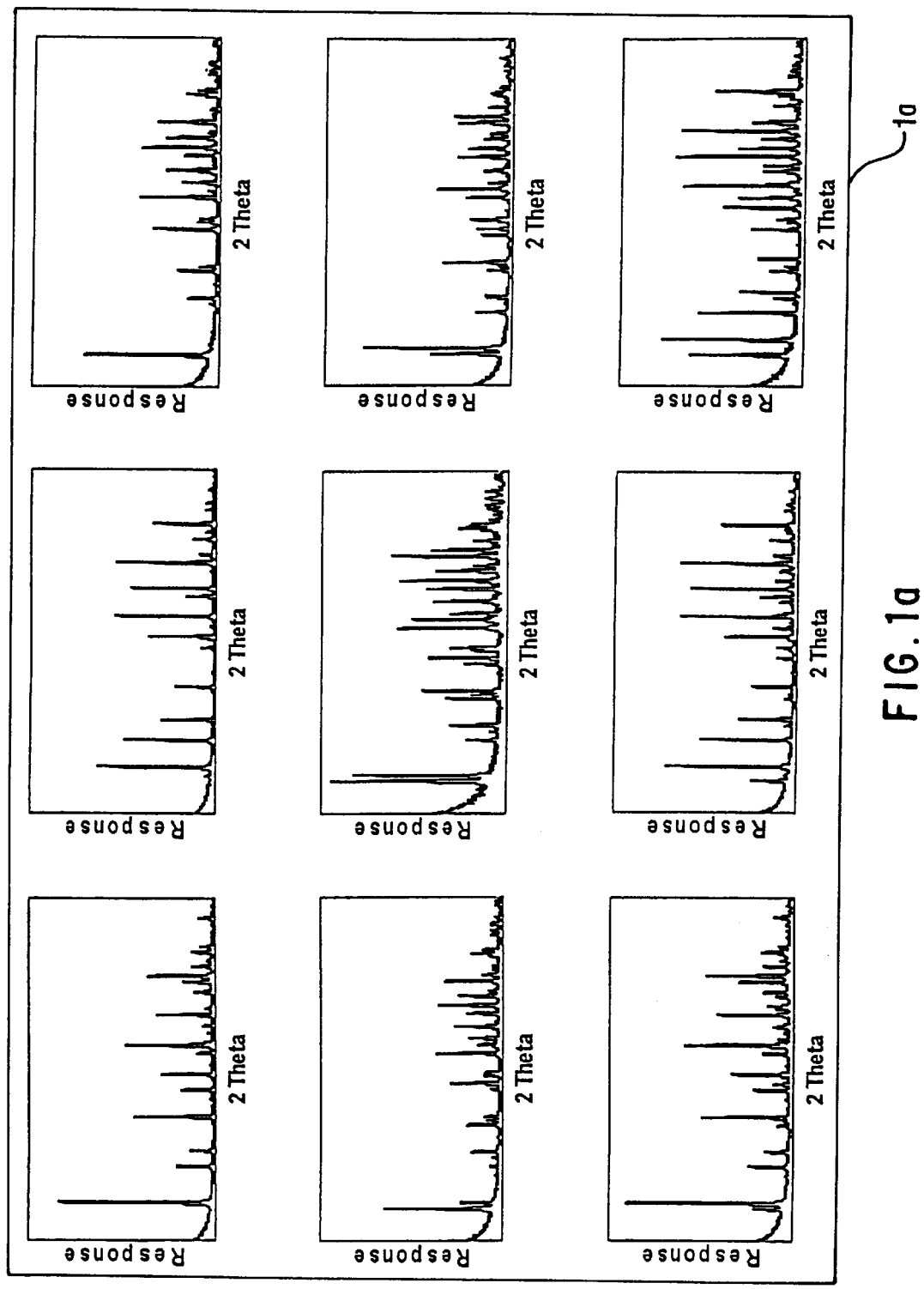
FIGS. 1a and 1b are a series of X-ray powder diffraction patterns corresponding to a set of samples containing the zeolites FAU, LTL, LTA and mixtures thereof.

This invention is applicable to any set of compounds whose structure may be analyzed by X-ray powder diffraction. The nature of the chemical reactions used to produce the compounds being analyzed is not critical. The invention provides the greatest benefit, however, when large numbers of compounds are being synthesized and require analysis such as in a combinatorial chemistry application. For example, in a combinatorial chemistry application, compounds may be generated in a set of 48, 96, or even 384 compounds simultaneously. Just a few combinatorial chemistry experiments may result in 1000 or more samples to analyze. A preferred analytical method in general use to identify the structure of such samples is X-ray powder diffraction. However, X-ray powder diffraction patterns are generally complex and require significant time and skill to interpret. The generation of 1000 or more samples for individual analysis on a daily basis, or even a weekly basis, would easily overwhelm most analytical laboratories.

The basic feature of the present invention is that a significant amount of information about the compounds may be generated rapidly using statistical analyses without the need for laboriously interpreting each individual X-ray powder diffraction pattern to sequentially determine the structural identity of each sample. That is to say, given a set of samples prepared, for example, combinatorially, the traditional procedure would be to look at each X-ray powder diffraction pattern individually, develop an identification for that sample, and proceed to the next sample. In the combinatorial approach, or whenever large numbers of samples are generated, the likelihood is that many of the samples will be the same, or very similar, or will at least be mixtures of a few pure compounds-. Consequently, much time will be spent interpreting X-ray powder diffraction patterns representing samples which are in fact the same. If one were capable of viewing hundreds of X-ray powder diffraction patterns simultaneously, and absorbing the details of each, one's preference would be to group together patterns which are the same or very similar, and only analyze one of these representative patterns to identify the structures they represent. However, as mentioned above, X-ray powder diffraction patterns consist of hundreds of data points and are too complex to be taken in, especially by the tens or hundreds of patterns at the same time.

PCA provides a method for carrying out this grouping of samples, thereby reducing the analyst's job from one of interpreting hundreds of patterns to the very much simpler task of only identifying the structures of the much fewer clusters identified. Furthermore, each cluster identified can be subjected to further analysis to generate subdlusters of even more similar materials which are present within these original clusters. The process of the invention begins by taking X-ray powder diffraction patterns of the samples in a set. X-ray powder diffraction techniques are well known in the art and will not be discussed in detail here. Greater detail may be found in texts such as Whiston, C, *X-Ray Methods*; Prichard, F. E., Ed.; Analytical Chemistry by Open Learning; John Wiley & Sons; New York, 1987, and *X-Ray Spectrometry*; Herglotz H. K., Birks, L. S. Eds.; Practical Spectroscopy Series, Vol. 2; Marcel Dekker: New York, 1978. The X-ray technique or instrumentation used is not critical to the success of the invention, but it is preferable that for a given set of samples, the same X-ray technique and instrumentation be used for each sample in the set (unless the intention of the analysis is to identify instrumental differences contributing to the XRD patterns for the set of samples). The X-ray powder diffraction pattern of any sample is generally expressed as a 2-dimensional representation of the intensity of the diffracted or scattered X-ray radiation at a particular $2\theta$ vs. the $2\theta$ value. That is, one axis represents intensity, the other the $2\theta$ diffraction angle. Whatever the details, each X-ray powder diffraction pattern may be viewed as a vector.

The patterns are then subjected to the well-known statistical technique of principal component analysis, to afford a small number of principal components, or factors, which reflect the predominant variations in the X-ray powder diffraction patterns among the samples considered. In other words, the principal components, which represent the major contributions to the pattern changes, are obtained from the samples by principal component analysis (or the related statistical techniques of SIMCA or Partial Least Squares). Thereafter, any new sample in this set, or any new sample subsequently scanned can be assigned various contributions of these principal components which would approximately reproduce its pattern. The amount of each principal component required is called its score, and it is these scores which are plotted for visual inspection. In mathematical terms, for a set of patterns denoted by the matrix X, the use of principal component analysis, for example, generates a set of principal component "loadings," P (which represent contributing spectral components) as eigenvectors of the equation $(X'X)P=PT$, and a scores matrix, T, such that $X=TP'$. For the purposes of the process envisioned in this application, only two to about five principal components are typically considered at a time to accommodate the data for a large range of compounds from a variety of chemical reactions. Although two to about five factors may not be sufficient to reflect the entire range of compounds represented in the data, this number of score dimensions are easily visualized and have proven satisfactory in practice for identifying clusters and outliers for the cluster/sub-cluster method described previously and again in more detail below. The X-ray powder diffraction pattern of the sample is then represented by the scores of the principal components used. It is the scores that are plotted and visually inspected as discussed below. Thus, no pattern matching between the sample X-ray powder diffraction patterns and known libraries of chemical and structural patterns need be conducted to gain significant amount of information. In fact, the nature of the sample itself need not be known; what is important is that the X-ray powder diffraction patterns of the samples be measured, that a set of principal components be identified for the set of samples, and that the scores for each X-ray powder diffraction pattern be determined and plotted.

Once the scores for each of the X-ray powder diffraction patterns have been determined, the scores are plotted on a graph. The number of principal components used also indicates the type of plot for the scores. For example, if 2 principal components or factors are used, the scores are plotted on a 2-dimensional graph, if 3 principal components are used, the scores are plotted on a 3-dimensional graph, and multiple graphs or multi-dimensional visualization programs such as SeeIT, available from Visible Decisions, can be used to represent higher numbers of dimensions. The PCA scores may be generated and plotted using any of the available multivariate statistical packages such as Pirouette, available from Infometrix, or UnScrambler, from Camo. The scores, once generated, may also be viewed using any of a number of multivariate visualization programs such as SeeIT, available from Visible Decisions; SpotfirePro, available from Spotfire; or AVS Express, available from Advanced Visual Systems.

The graph of the scores is then inspected, typically visually by an analyst, but it is contemplated that other algorithms may be used to analyze the clustering and patterns of the scores. A surprising amount of information is gathered from the graph. For example, the closer the two scores are to one another on the graph, the more similar the two samples are to one another, especially when using the scores for the first two or three principal components or factors. Conversely, when a unique material is present, i.e., a potentially new compound, its score typically falls at some distance from the main clusters, i.e., it is an "outlier", thus new materials are much easier to detect in a large set of samples. Or, to turn a phrase, the needle becomes displaced from the haystack. Scores for similar materials cluster together on the graph, and if the identity of one of the samples in that homogeneous cluster is known, then the identity of the rest of the samples in the cluster is also known. The time and labor savings from noting clusters can be enormous. For example, in the case where 100 samples are subject to the process of the invention as described above and the resulting plotted scores fall into three distinct clusters (which do not show the presence of subclusters when analyzed further), only three of the X-ray powder diffraction patterns would need to be further processed using a search and match program in combination with a library of known X-ray powder diffraction patterns. The results of the first search and match routine can be extrapolated to each of the X-ray powder diffraction patterns in the cluster from which the first representative X-ray powder diffraction pattern was taken. The results of the second search and match routine can be extrapolated to each of the X-ray powder diffraction patterns in the cluster from which the second representative X-ray powder diffraction pattern was taken, and so on. For the time and effort needed to particularly identify three X-ray powder diffraction patterns, the identity of all 100 samples can be estimated with reasonable certainty. Similarly, novel structures can be detected by the failure of the comparison of a sample X-ray powder diffraction pattern to known X-ray powder diffraction patterns to result in a match. The novel structure detected for one sample in a cluster may be extrapolated to each of the X-ray powder diffraction patterns in the cluster from which the representative X-ray powder diffraction pattern was taken.

As mentioned above, the plots of the scores may be inspected visually or using statistical pattern recognition programs to determine characteristics such as clusters and outliers. Suitable statistical techniques include K-nearest neighbors, Mahalanobis distances, and density mapping to identify the characteristics. Additional clustering methods that may be used in inspecting the plots of the scores include Jardine and Sibson's node analysis, Forgy's method of centroids, MASLOC method of centrotypes, fuzzy clustering, Minimum spanning tree method, and McQueen's K-means method, see *Chemometrics: A Textbook*, D.L. Mossart, et al. Elsevier, 1998 pp. 371–383, 392–399, 431.

To aid in identifying the structural nature of the samples within a cluster, known samples may be contained as part of the sample set. The known samples would be analyzed along with the rest of the sample set as described above. The position of the scores of the known samples on the graph of the scores would help to identify compositions represented by clusters or possibly outliers. For example, if a known sample lies within a particular distinct cluster, it is a good indication that the rest of the samples in that cluster have a structural identity very close to that of the known sample. The reason for this is that the X-ray powder diffraction patterns for the known material closely matches the X-ray powder diffraction patterns for the other samples in the cluster. Consequently, when the scores for the cluster samples and the known sample are computed, they will be very similar.

Equally as important is the opportunity for an analyst to single out and focus on those samples whose plotted scores do not fit into any of the clusters. Such data points are termed "outliers". Outliers are generally either new materials or perhaps faulty data. In either case, these few outlier samples can be studied in more detail while a majority of the samples can be safely assigned to known categories. Again, the potential time and labor savings to an analyst can be significant. Those X-ray powder diffraction patterns offering the greatest potential for representing new materials are identified and may be focused on without expending resources on X-ray powder diffraction patterns associated with less promising materials.

The plot of the scores may also indicate the transition of one phase into another or the presence of two or more phases in a single sample. Thus, to the extent that X-ray powder diffraction patterns are approximately additive for mixtures of pure powder, the scores for the mixture will also be linear averages of the scores for the pure materials, approximately weighted by the proportions of each. For example, the score for a mixture of 50% A and 50% B will be approximately midway between the scores representing pure A and pure B. On the other hand, the score for a sample comprised of 20% A and 80% B will lie on the line between the scores for the two pure materials but only about one-fifth of the way from B to A. The score for a mixture of three pure phases would line on the plane formed by the scores for the three pure phases.

Additional information may be obtained by repeating the analysis portion of the above method one or more times on successively smaller subsets of samples. For example, in a specific embodiment of the invention, a cluster may be noticed on the graph of the scores. Those samples making up the cluster may be selected as a subset and the principal component analysis may be applied to the subset alone. Additional X-ray powder diffraction patterns need not be generated, the principal component analysis may be applied to the patterns generated originally. The principal components, which represent the major contributions to the pattern changes within this subset, are obtained from the subset of selected samples by principal component analysis (or SIMCA or Partial Least Squares). The PCA scores for each sample in the subset are determined and plotted as described above. Again the graph of the scores is examined for clustering, outliers, or trends (which may represent transitions or multiple phases). Using principal component analysis and plotting the scores of a smaller subset of samples may result in previously undetected differences within the subset becoming apparent. In other words, whereas with the full sample set, the cluster may have appeared to be very closely related, a closer inspection of just the samples making up the cluster alone may resolve sub-clusters or other useful information. Such iterations of progressively smaller subsets of samples being analyzed may yield additional information and may be continued until no additional useful information is contained in the data. The stopping point may occur when the analyst sees no variations among the overlaid patterns of the samples within that cluster, or it may be determined by the uniform density or randomness of the scores for that subset when plotted.

To aid in determining whether a cluster should be resolved into sub-clusters, an overlay of all the X-ray powder diffraction patterns corresponding to the samples making up the cluster may be inspected. If the overlay of all the patterns shows differences, then sub-clustering and principal component analysis of only this cluster, with plotting of the scores as described above, may result in a greater degree of information.

Without intending any limitation on the scope of the present invention and as merely illustrative, examples of this invention are provided below in specific terms as applied to specific embodiments of the invention. The examples clearly show the methodology and the benefits of the approach described herein.

EXAMPLE 1

Three different zeolites were synthesized and mixtures of the zeolites were prepared. The sample set contained samples having the weight ratios of the zeolites as shown in Table 1. Zeolite designations are according to the standards set by the Structure Commission of the International Zeolite Association; see Meier, W. M.; Olson, D. H.; *Baerlocher Atlas of Zeolite Structure Type*, 4th Revised Ed.; Rees, V. C., von Ballmoos, R. Eds.; Published on Behalf of the Structure Commission of the International Zeolite Association; Elsevier: N.Y., 1996, pp 104–105 and pp 130–133. FAU refers to faujasite, LTL refers to Linde Type L, and LTA refers to Linde Type A.

TABLE 1

| Sample No. | % FAU | % LTL | % LTA |
|---|---|---|---|
| 1 | 100 | 0 | 0 |
| 2 | 0 | 100 | 0 |
| 3 | 0 | 0 | 100 |
| 4 | 20 | 60 | 20 |
| 5 | 60 | 20 | 20 |
| 6 | 20 | 20 | 60 |
| 7 | 20 | 80 | 0 |
| 8 | 40 | 60 | 0 |
| 9 | 60 | 40 | 0 |
| 10 | 80 | 20 | 0 |
| 11 | 0 | 20 | 80 |
| 12 | 0 | 40 | 60 |
| 13 | 0 | 60 | 40 |
| 14 | 0 | 80 | 20 |
| 15 | 20 | 0 | 80 |
| 16 | 40 | 0 | 60 |
| 17 | 60 | 0 | 40 |
| 18 | 80 | 0 | 20 |

Figure 1B:
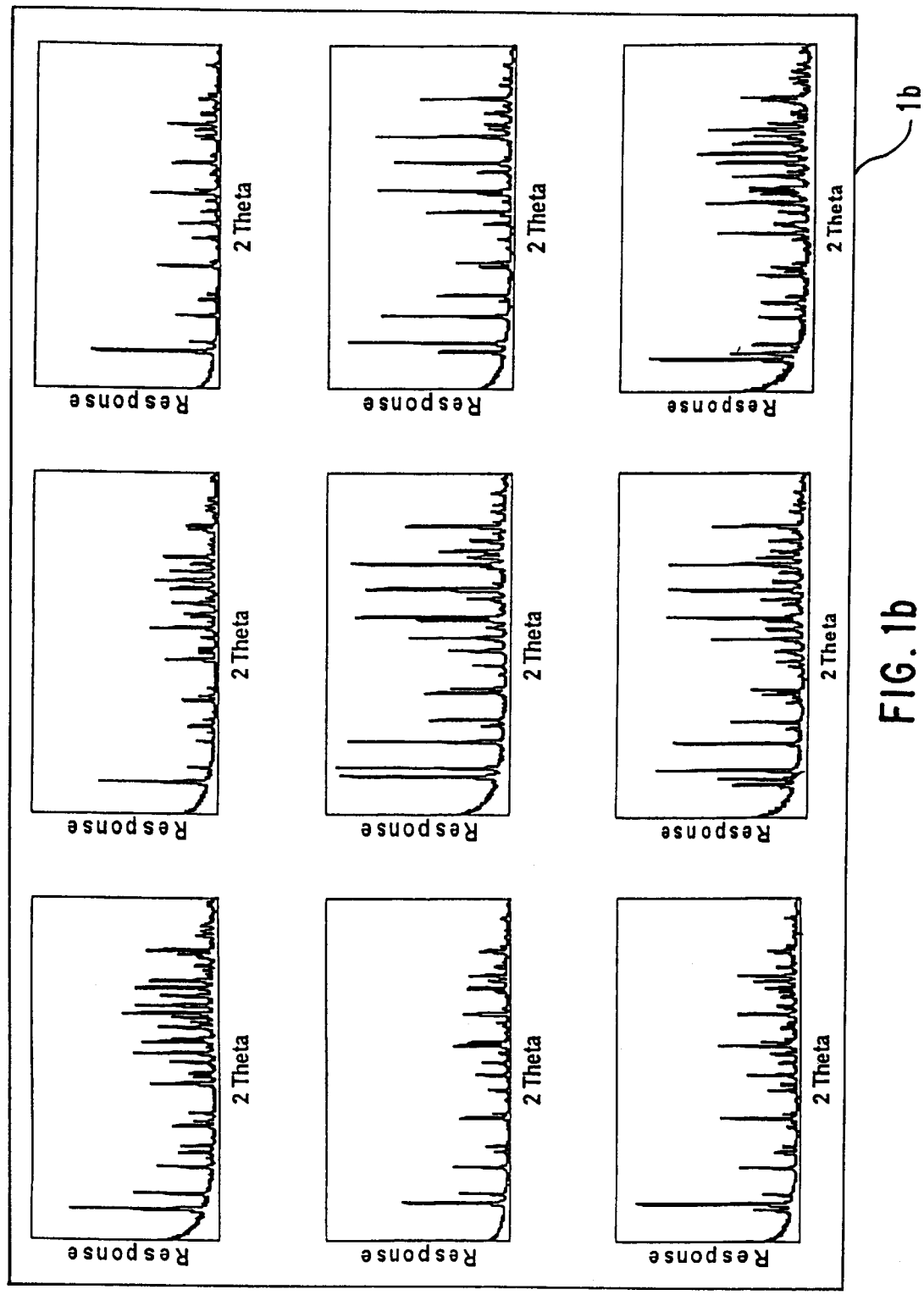
Figure 3:
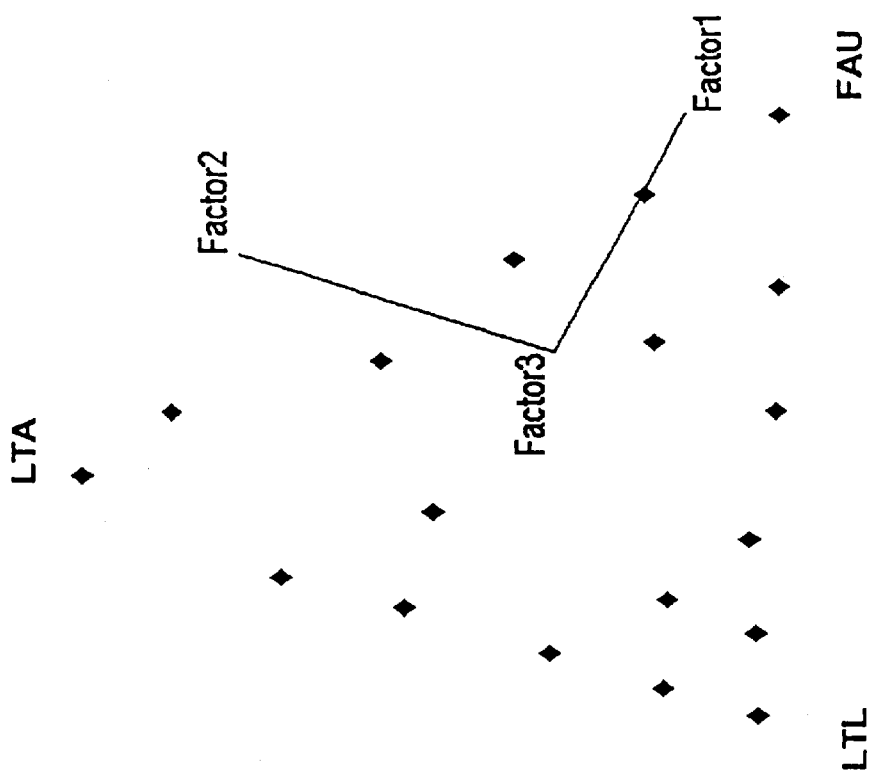
FIG. 3 is a 3-dimensional graph of the scores resulting from applying principal component analysis to the X-ray powder diffraction patterns of FIGS. 1a and 1b, which corresponds to the samples in FIG. 2, to determine a number of factors and calculating the scores of each factor for each X-ray powder diffraction pattern of the sample set.
Figure 2:
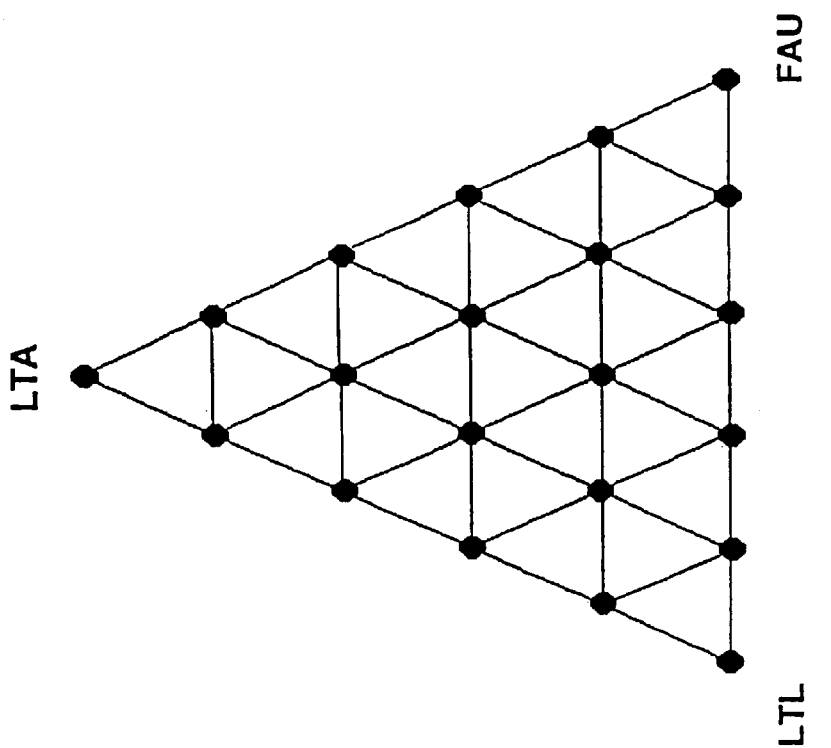
FIG. 2 is a ternary phase diagram of FAU, LTL, LTA and mixtures thereof used to generate an example test set.

The X-ray powder diffraction pattern was obtained for each sample in the sample set using Scintag Theta-Theta having a copper radiation source. FIGS.1*a* and 1*b* show the X-ray powder diffraction patterns of the samples and demonstrate that when the X-ray powder diffraction patterns are viewed individually, it is hard to distinguish any correlation. The set of X-ray powder diffraction patterns was then analyzed using principal component analysis to determine three factors. From the factors, the scores for each sample in the sample set were then calculated and plotted in a 3-dimensional graph. FIG. 2 shows the phase diagram marked with the sample compositions used. FIG. 3 shows the plot of the scores calculated for the corresponding samples. A comparison of FIG. 2 and FIG. 3 clearly shows that the plot of the scores closely resembles the phase diagram. In FIG. 3, the pattern of the plotted scores is triangular with the pure phases at the corners of the triangle. The scores for the remaining samples fell within the triangle in such as way as to indicate the various mixtures and the approximate amounts of each zeolite, thus demonstrating that principal component analysis may be successfully used to analyze X-ray powder diffraction patterns. That is to say that PCA can not only analyze samples consisting of pure phases, but can also distinguish between samples containing various mixtures of those pure phases. Moreover, the scores for the mixtures are seen to lie on tie lines between the scores for the pure phases.

EXAMPLE 2

Figure 4:
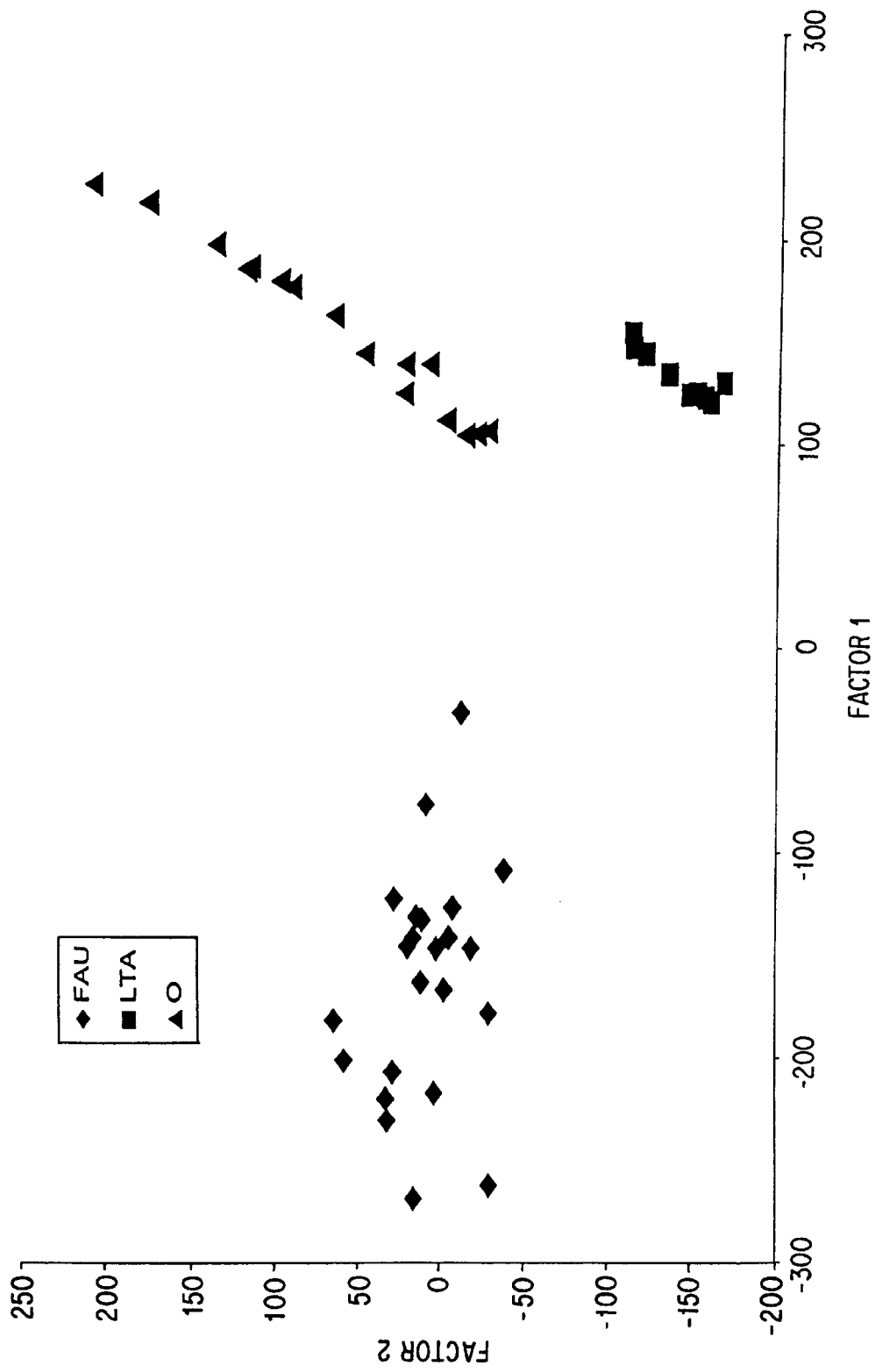
FIG. 4 is a 2-dimensional graph of the scores resulting from applying principal component analysis to the X-ray powder diffraction patterns of a random set of samples which consist of FAU, LTA, or blanks to determine a number of factors and calculating the scores of each factor for each X-ray powder diffraction pattern.

Blanks and standard samples of the zeolites FAU and LTA were analyzed by X-ray powder diffraction to obtain the X-ray powder diffraction patterns using standard X-ray powder diffraction techniques. The diffractometer used was a Brucker AXS D8 Advance. The radiation source was a high intensity X-ray tube operated at 40 kV and 40 ma. The diffraction pattern from the copper K-alpha radiation was obtained by appropriate computer based techniques. Flat powered samples were continuously scanned at $3.6°(\theta)$/min from $5°$ to $40°(\theta)$. Principal component analysis was applied to all the X-ray powder diffraction patterns and four factors were determined. The scores of the factors for each of the samples and blanks analyzed were calculated and plotted on 2-dimensional graphs. The resulting plot of the scores for the first two factors is shown in FIG. 4. A visual inspection of FIG. 4 readily demonstrates three clusters of scores. One cluster was verified as FAU, another was verified as LTA, and the third was verified as the blanks.

Figure 5:
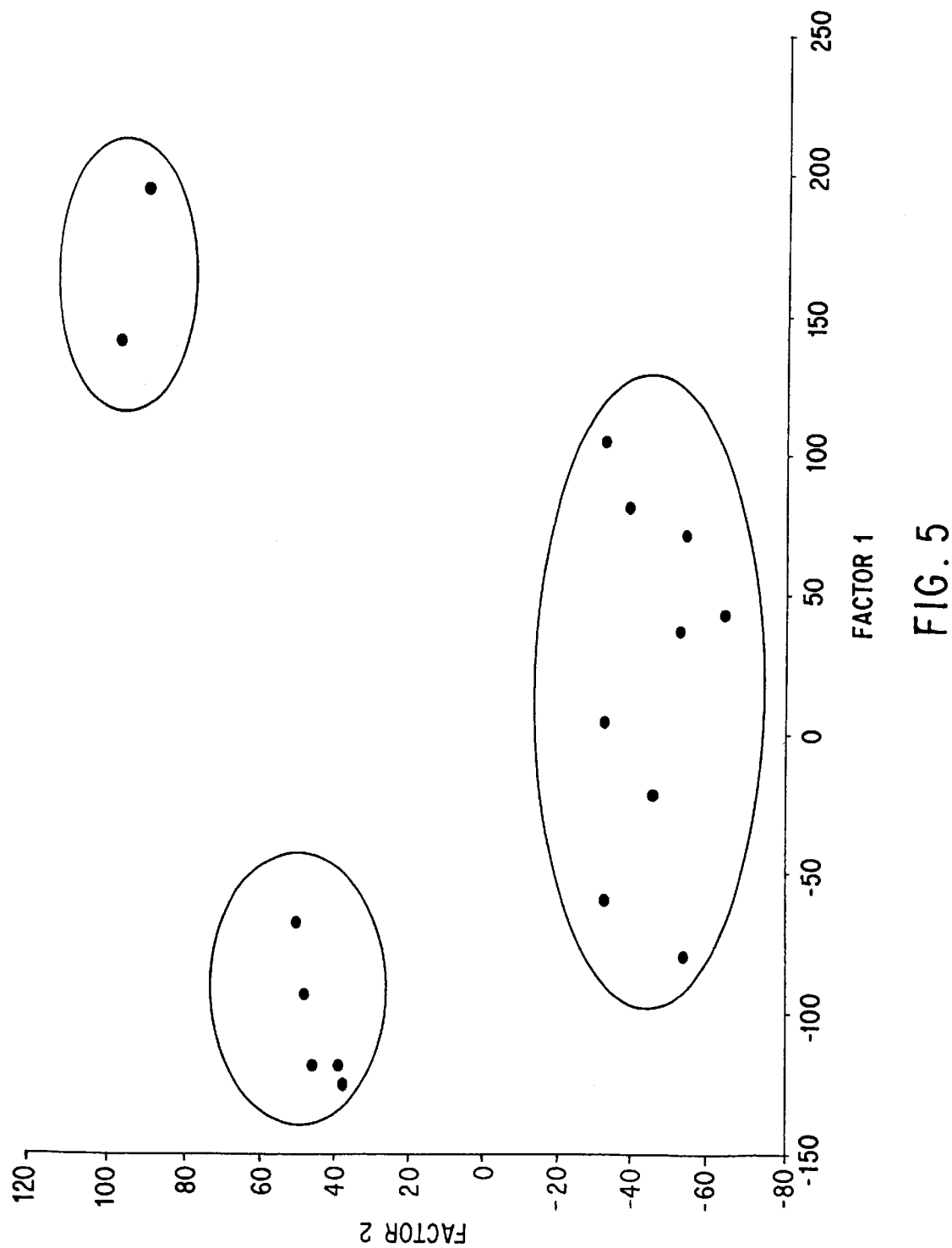
FIG. 5 is a 2-dimensional graph of the scores resulting from applying principal component analysis to the X-ray powder diffraction patterns of the sub-cluster of blanks from FIG. 4 to determine a number of factors and calculating the scores of each factor for each X-ray powder diffraction pattern in the cluster of blanks of FIG. 4
Figure 6A:
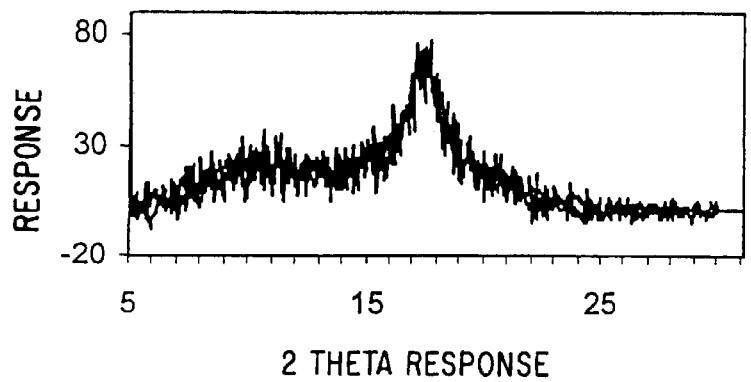
FIG. 6a, 6b and 6c contains overlaid X-ray powder diffraction patterns, for each of the clusters of FIG. 5. The three clusters of blank samples correspond to three types of artifacts associated with the blank sample cell.
Figure 6B:
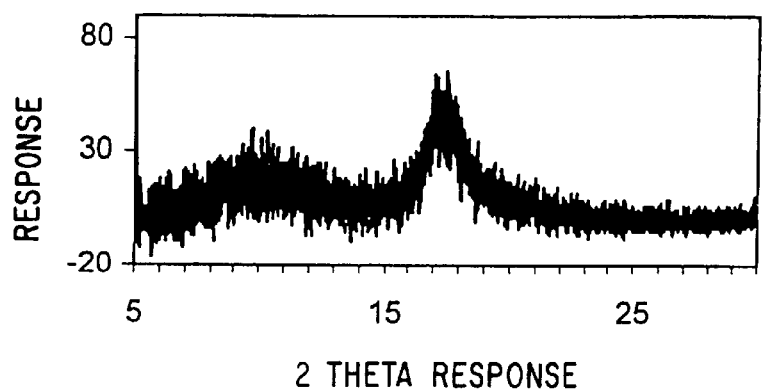
Figure 6C:
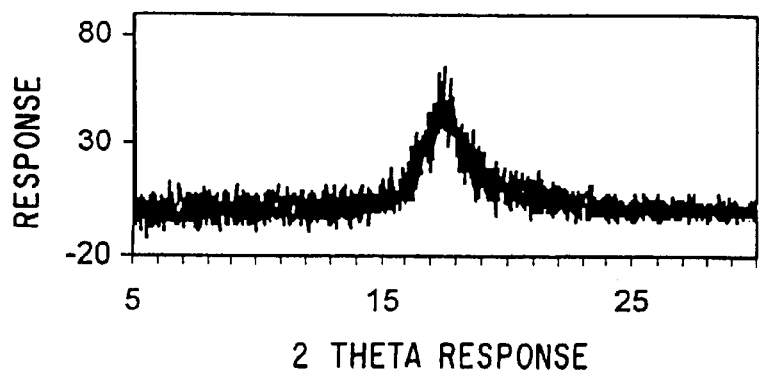

The cluster of blanks appeared visually to be elongated. Therefore, principal component analysis was applied to those X-ray powder diffraction patterns corresponding to the blanks shown in FIG. 4 and four factors were determined. The scores of the factors for each of the blanks analyzed were calculated and plotted on 2-dimensional graphs. The resulting plot of the scores for the first two factors is shown in FIG. 5. A visual inspection of FIG. 5 readily demonstrated three clusters of scores within the subset of blank samples. Overlaid X-ray powder diffraction patterns for each of the three clusters of FIG. 5 are shown in FIGS. 6a, 6b and 6c. Inspecting the clusters of FIG. 5 enabled the analyst to determine that variations in the background material used to mount samples and plate alignment were resulting in different X-ray powder diffraction patterns for blanks. Therefore, PCA can not only be used to successfully discriminate between different sample compositions, but can also lead to the identification of erroneous data and the isolation of the causes of those errors.

EXAMPLE 3

Figure 7:
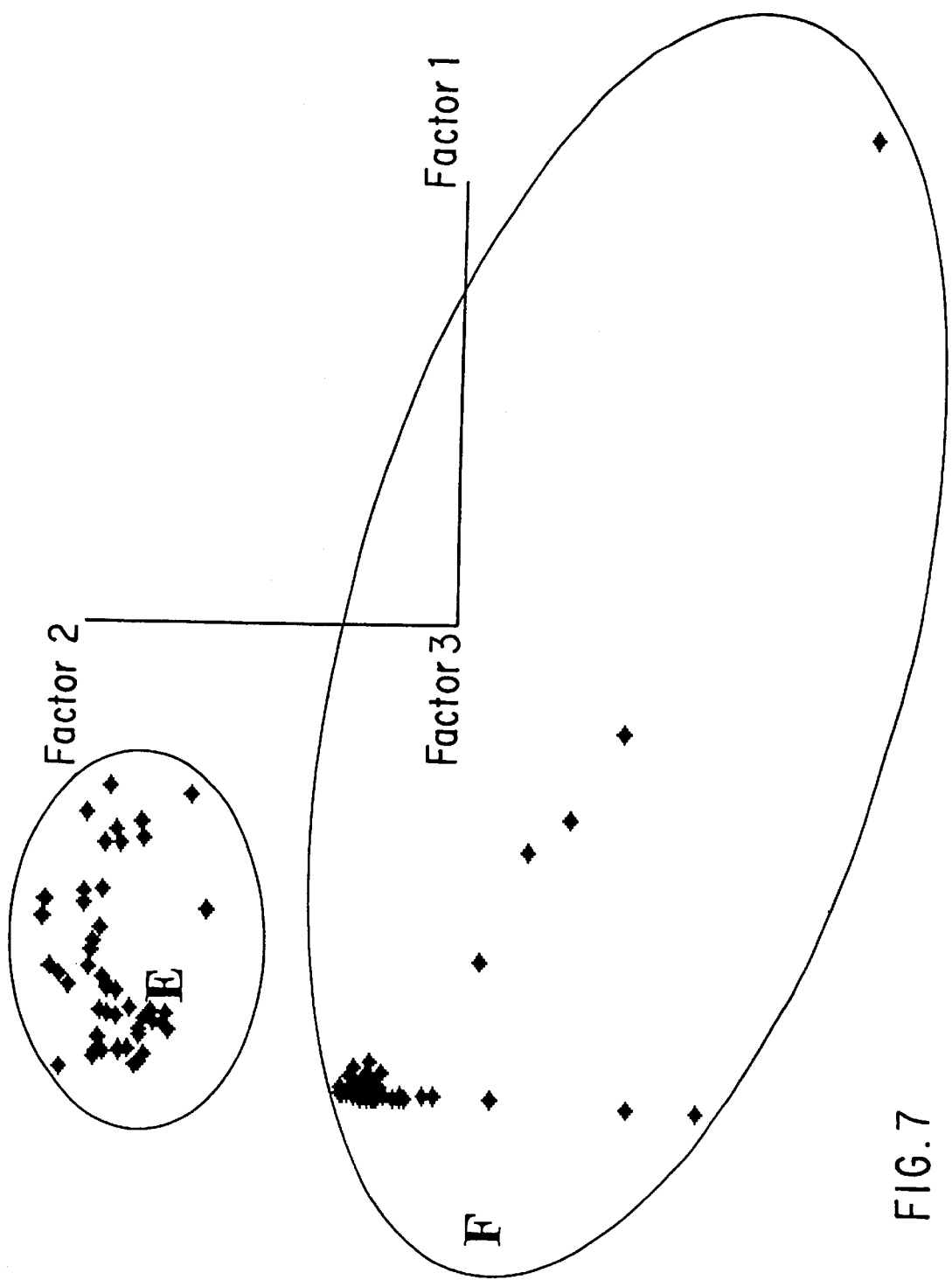
FIG. 7 is a 3-dimensional graph of the scores resulting from applying principal component analysis to the X-ray powder diffraction patterns of two subsets of samples prepared in the Cu—Zn—V—O system, one subset synthesized at 150° C. and the other subset synthesized at 200° C., to determine a number of factors and calculating the scores of each factor for each X-ray powder diffraction pattern.

A combinatorial approach was used to investigate the hydrothermal chemistry of the Zn—Cu—V—O system. The chosen formulations were investigated under various reaction conditions. One particular synthesis condition was digestion at 150° C. for seven days, and another was digestion at 200° C. for seven days. All of the resulting samples go were analyzed by X-ray powder diffraction to obtain the X-ray powder diffraction patterns. As in Example 2, the X-ray powder diffraction patterns were obtained using standard X-ray powder diffraction techniques. The diffractometer used was a Brucker AXS D8 Advance with a high intensity X-ray tube radiation source operated at 40 kV and 40 ma. The diffraction pattern from the copper K-alpha radiation was obtained by approximate computer based techniques. Flat powered samples were continuously scanned at $3.6°(\theta)$/min from $5°$ to $40°(\theta)$. Principal component analysis was applied to all the X-ray powder diffraction patterns and four factors were determined. The scores of the factors for each of the samples and blanks analyzed were calculated and the first three scores were plotted on a 3-dimensional graph. The resulting plot of the scores is shown in FIG. 7. A visual inspection of FIG. 7 readily demonstrated two distinct clusters of scores. The cluster labeled "E" was verified as the materials synthesized at 150° C. and the other cluster labeled "F" was verified as the materials synthesized at 200° C.

The cluster of samples synthesized at 200° C.contained several patterns that were unexpected. Therefore, principal component analysis was applied to those X-ray powder diffraction patterns corresponding to the subset of samples synthesized at 200° C.and four factors were determined. The scores of the factors for each of the samples were calculated and the first three scores were plotted on a 3-dimensional graph, shown in FIG. 8. A visual inspection of FIG. 8 readily demonstrates trending of scores within the subset. The trending was verified to represent samples that were quenched while undergoing a transformation between phases due to the high temperature. The trending of the scores correlated with changes in the intensities of certain peaks of the samples as the phase transformation occurred.

Figure 8:
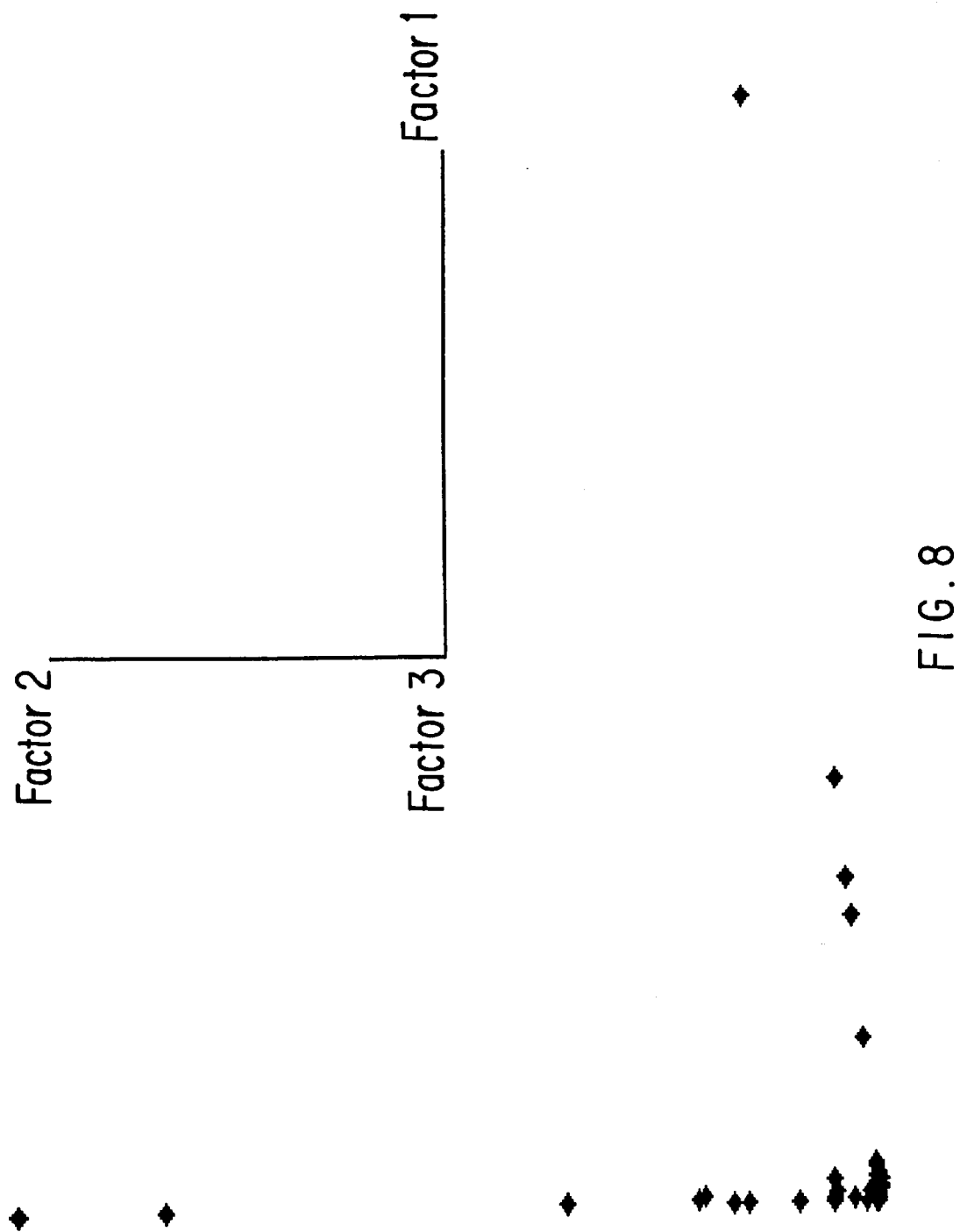
FIG. 8 is a 3-dimensional graph of the scores resulting from applying principal component analysis to the X-ray powder diffraction patterns of one subset of samples prepared in the Cu—Zn—V—O system synthesized at 200° C. to determine a number of factors and calculating the scores of each factor for each X-ray powder diffraction pattern.
Figure 9:
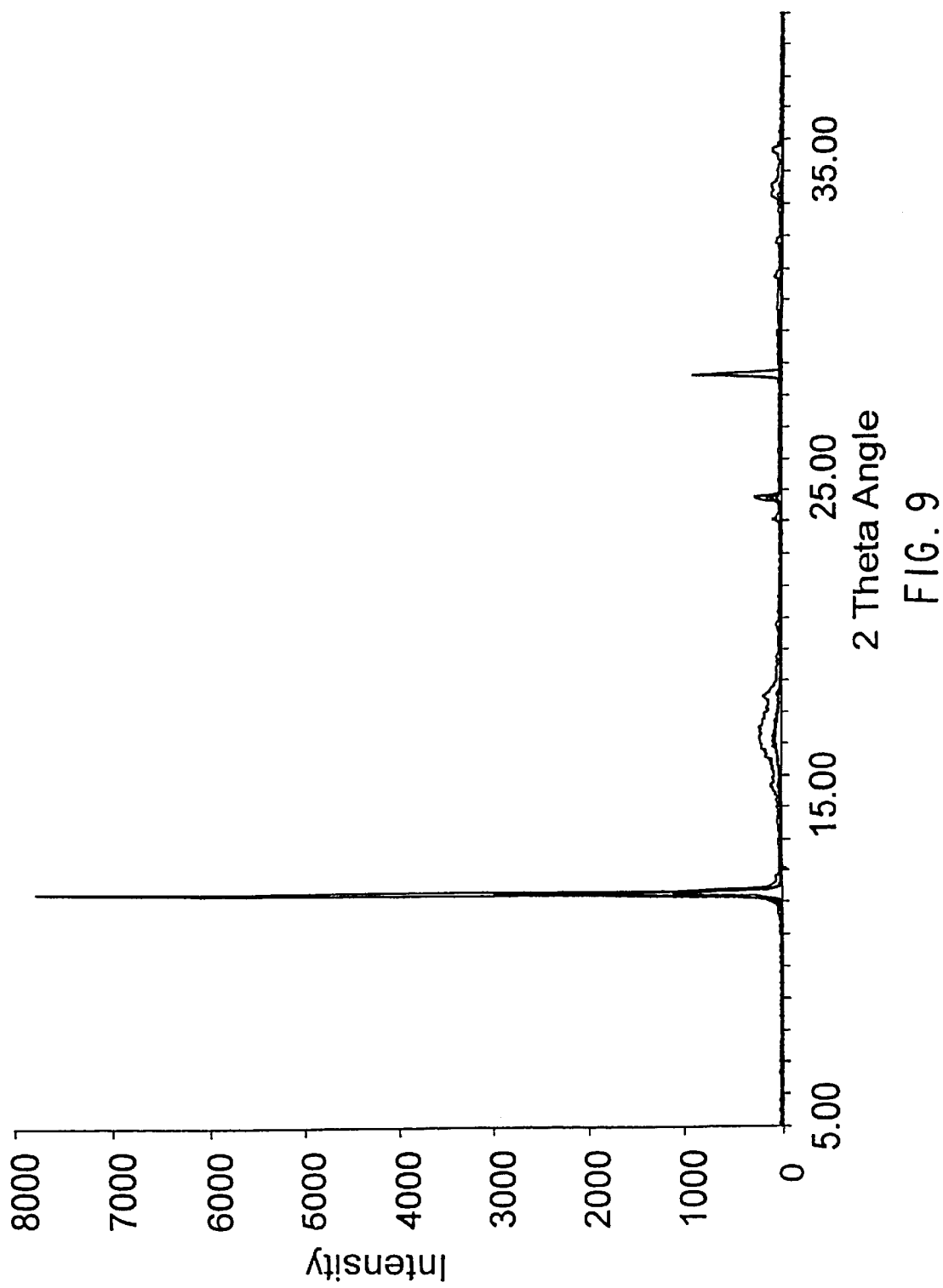
FIG. 9 is overlaid X-ray powder diffraction patterns corresponding to the five outliers along the Factor 1 axis of FIG. 8.
Figure 10:
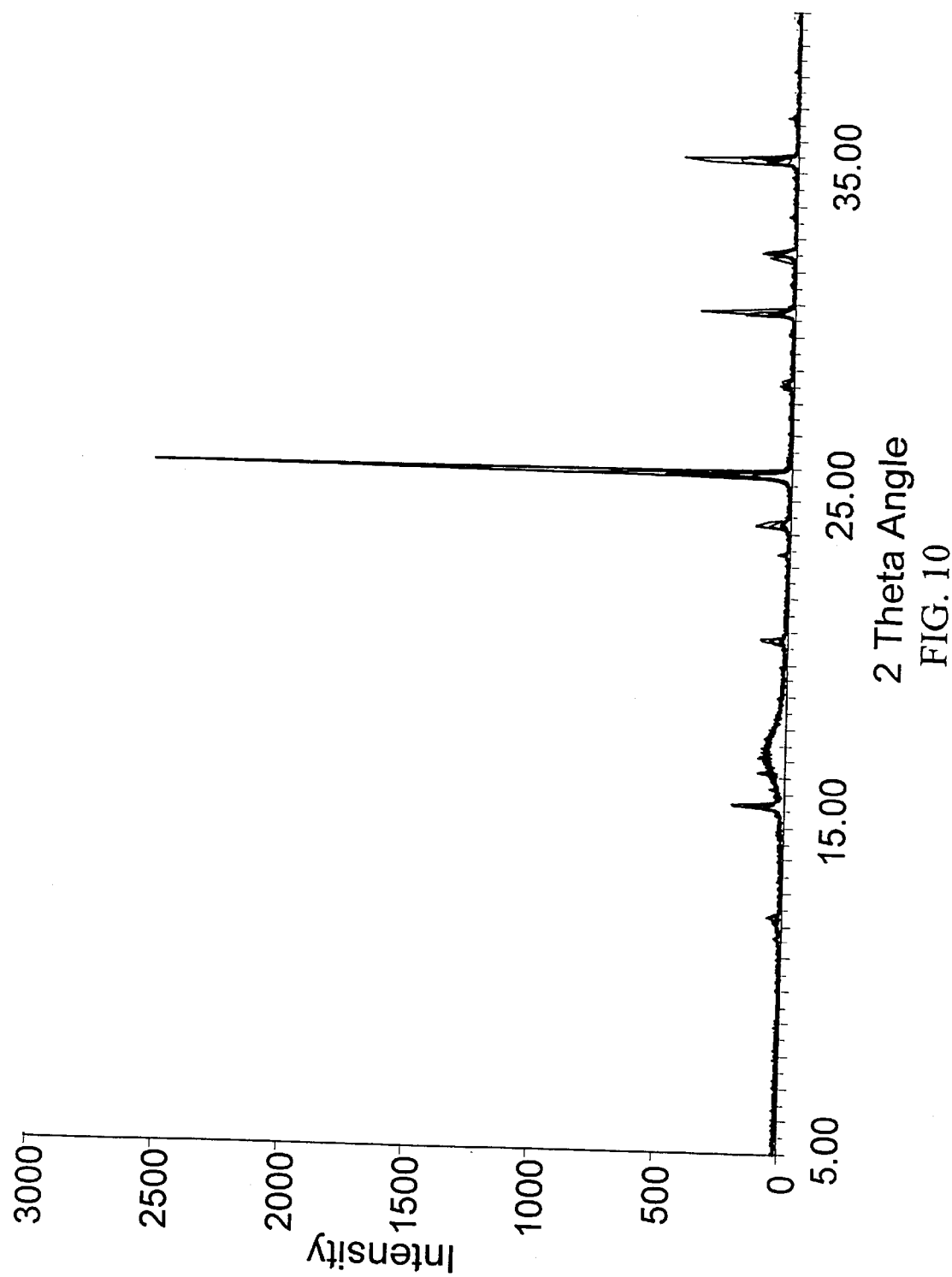
FIG. 10 is overlaid X-ray powder diffraction patterns corresponding to the eight outliers along the Factor 2 axis of FIG. 8.

A visual inspection of FIG. 8 shows a cluster with two branches of outliers radiating from it along the Factor 1 and Factor 2 axes. These samples were significantly different than the samples within the main or apical cluster and dominated the first three factors with respect to their importance. The five outliers along the Factor 1 axis were identified as a new material by X-ray powder diffraction analysis, and the new material was designated CuZnVO#15. The X-ray powder diffraction patterns for these five samples are shown in FIG. 9. Within this group of five outliers, the key difference was peak intensity. Likewise, the branch of eight outliers which fell along the Factor 2 axis was identified as a new material designated as ZnVO#13. The corresponding X-ray powder diffraction patterns for the latter set of samples are shown in FIG. 10. As before, the main difference among the patterns for this group of outliers was peak intensity.

Figure 11:
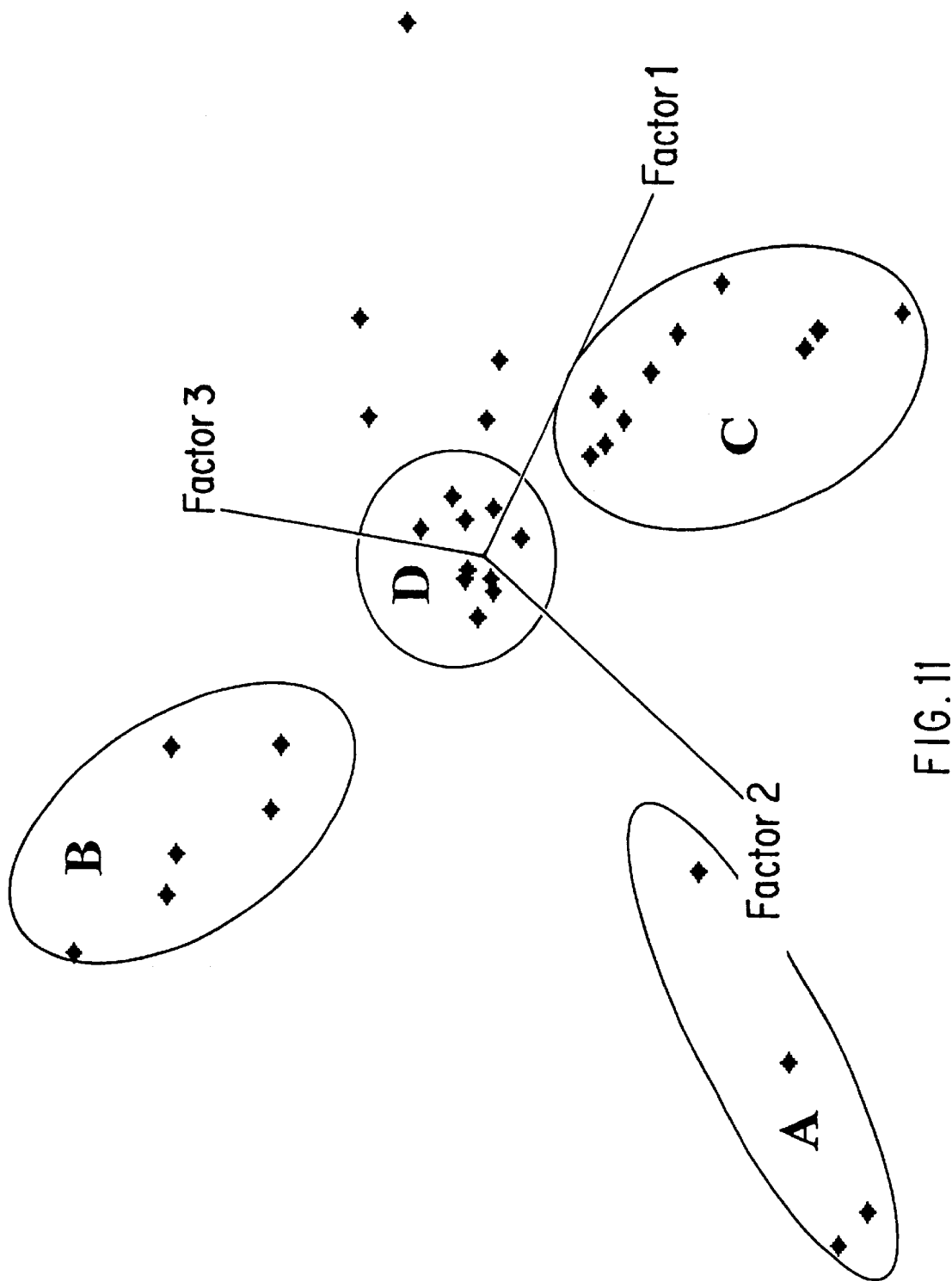
FIG. 11 is a 3-dimensional graph of the scores resulting from applying principal component analysis to the X-ray powder diffraction patterns of the remaining samples prepared in the Cu—Zn—V—O system after the two groups of outliers have been removed to determine a number of factors and then calculating the scores of each factor for each X-ray powder diffraction pattern.
Figure 12:
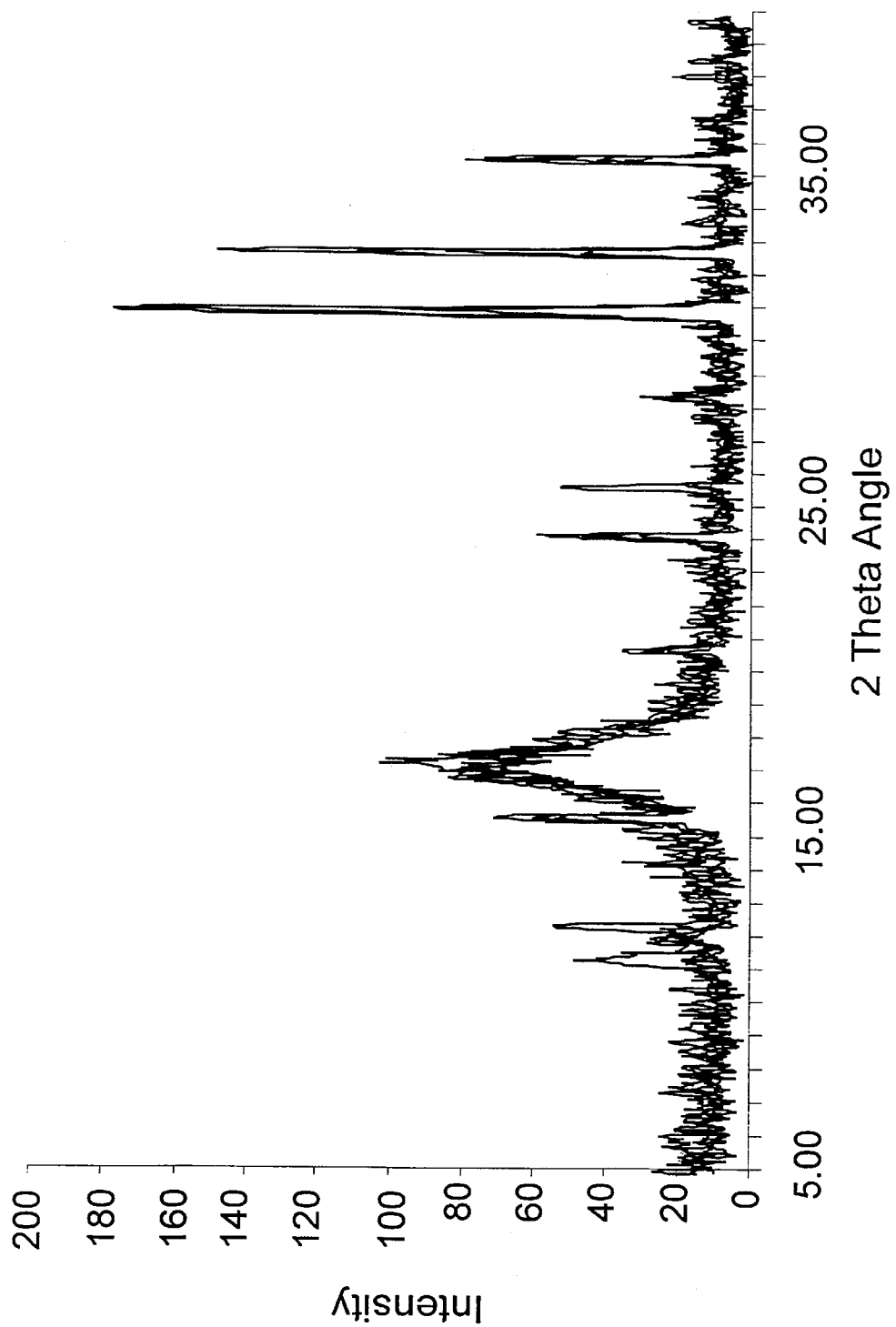
FIG. 12 is overlaid X-ray powder diffraction patterns corresponding to cluster A of FIG. 11.
Figure 13:
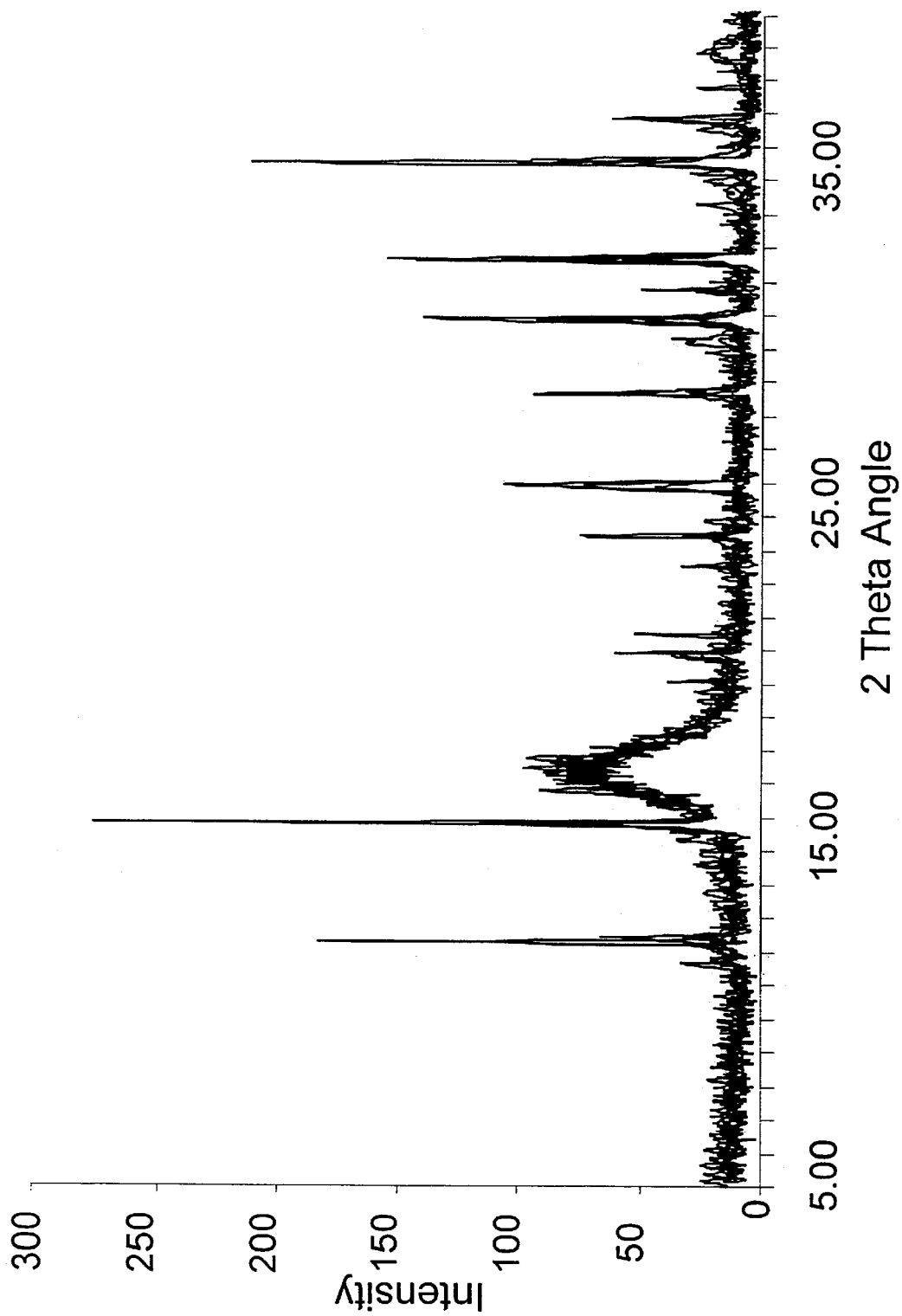
FIG. 13 is overlaid X-ray powder diffraction patterns corresponding to cluster B of FIG. 11.
Figure 14:
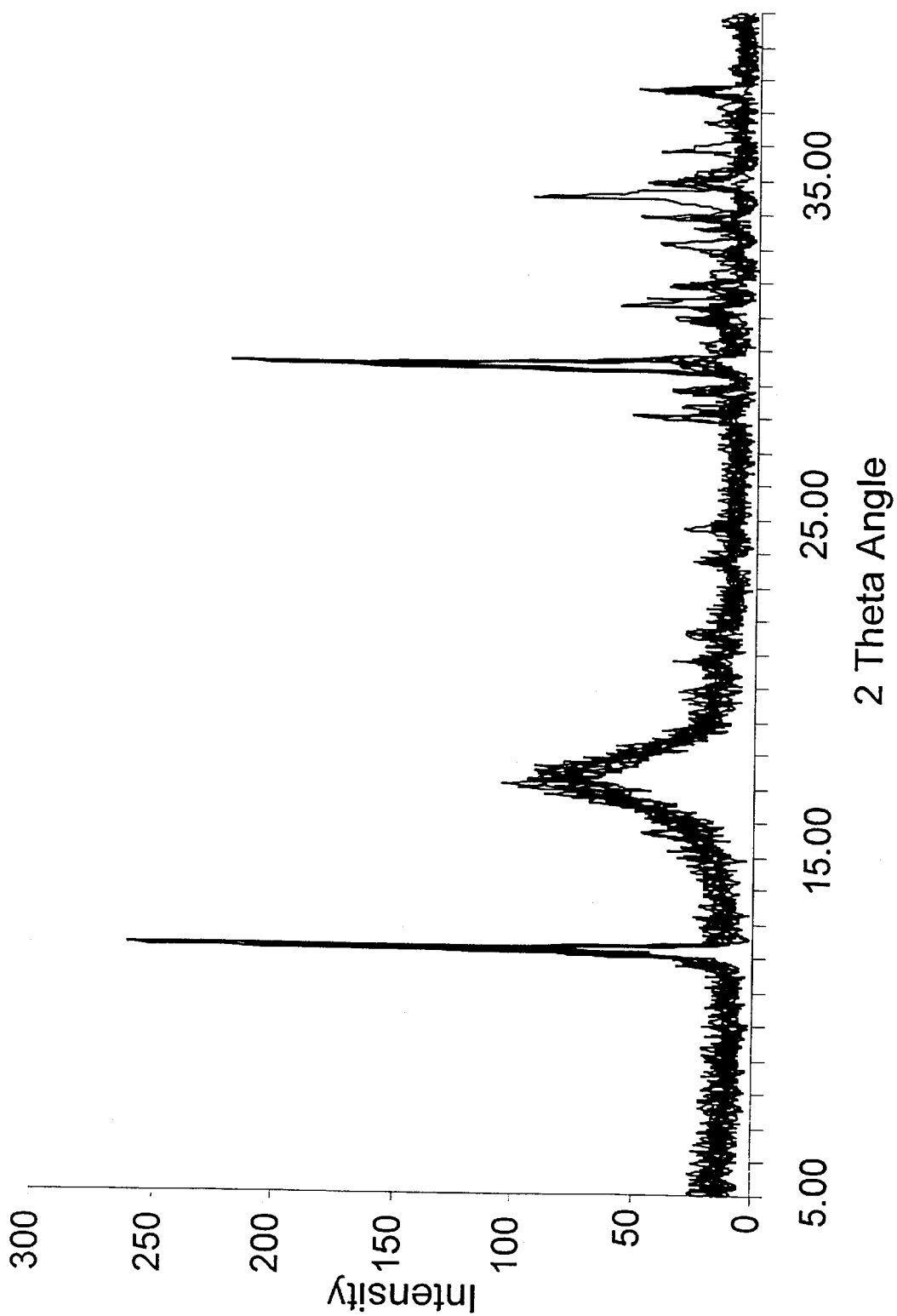
FIG. 14 is overlaid X-ray powder diffraction patterns corresponding to cluster C of FIG. 11.
Figure 15:
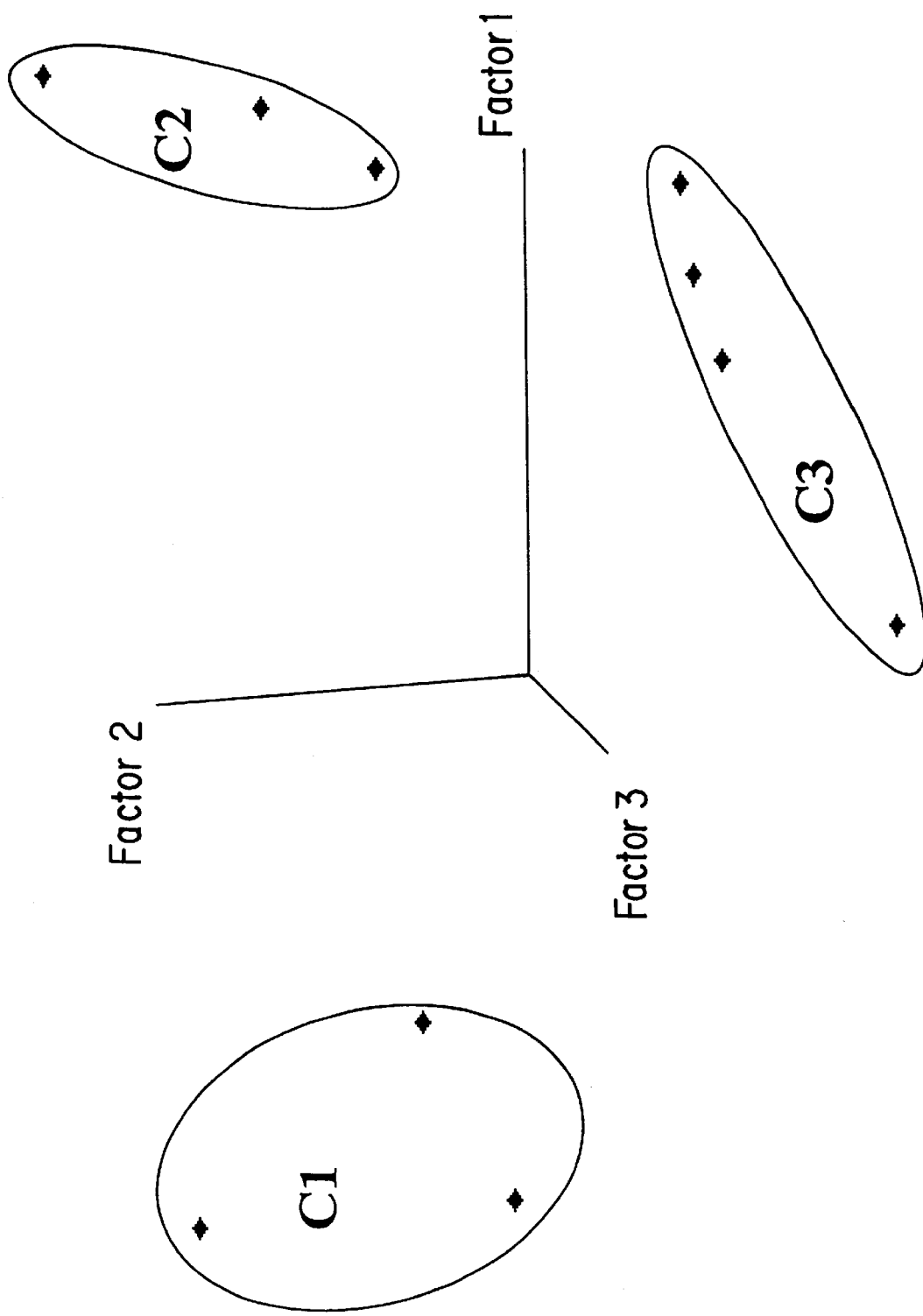
FIG. 15 is a 3-dimensional graph of the scores resulting from applying principal component analysis to the X-ray powder diffraction patterns of the sub-set of samples prepared in the Cu—Zn—V—O system labeled "C" in FIG. 11 to determine a number of factors and then calculating the scores of each factor for each X-ray powder diffraction pattern.
Figure 16:
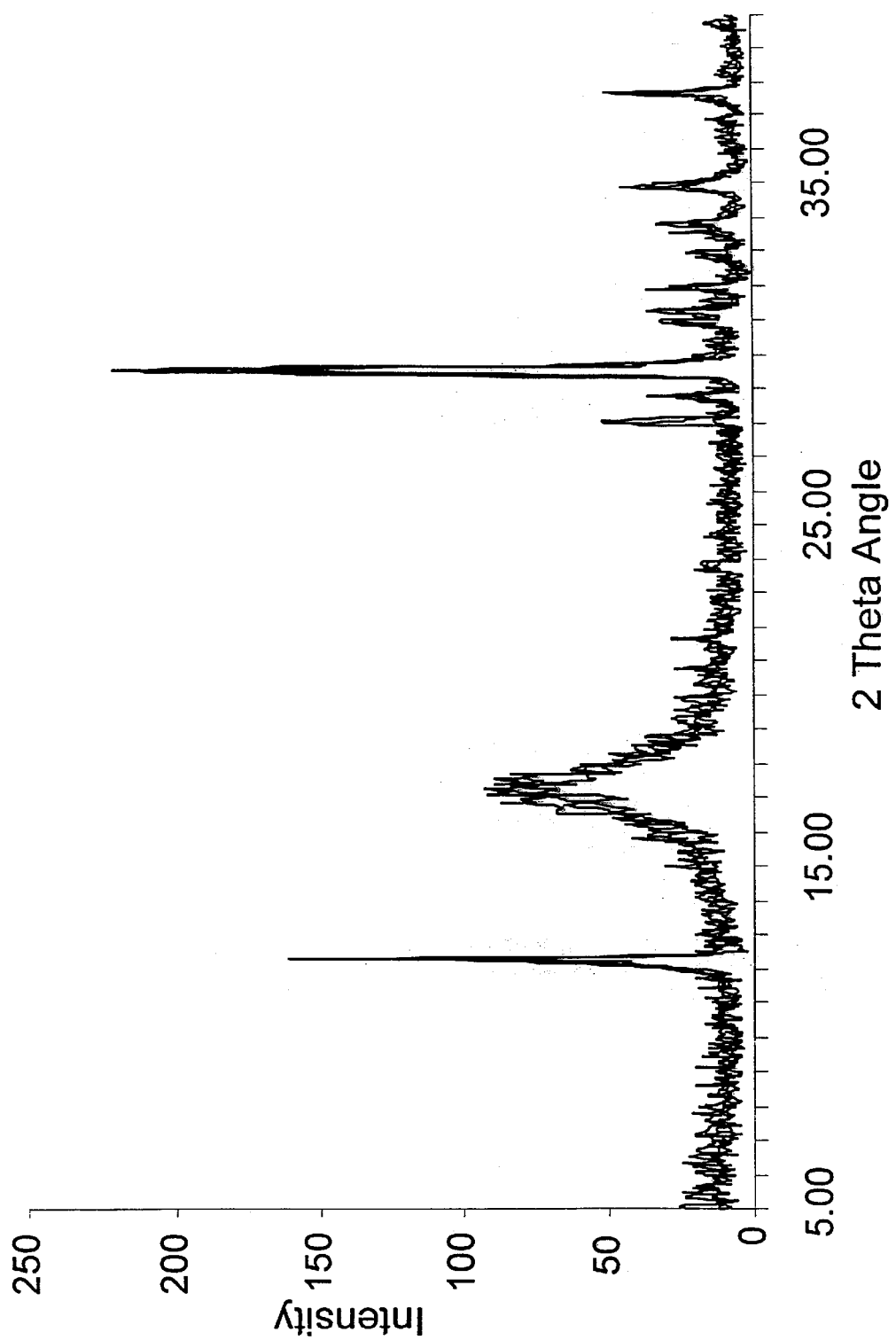
FIG. 16 is overlaid X-ray powder diffraction patterns corresponding to cluster $C_1$ of FIG. 15.
Figure 17:
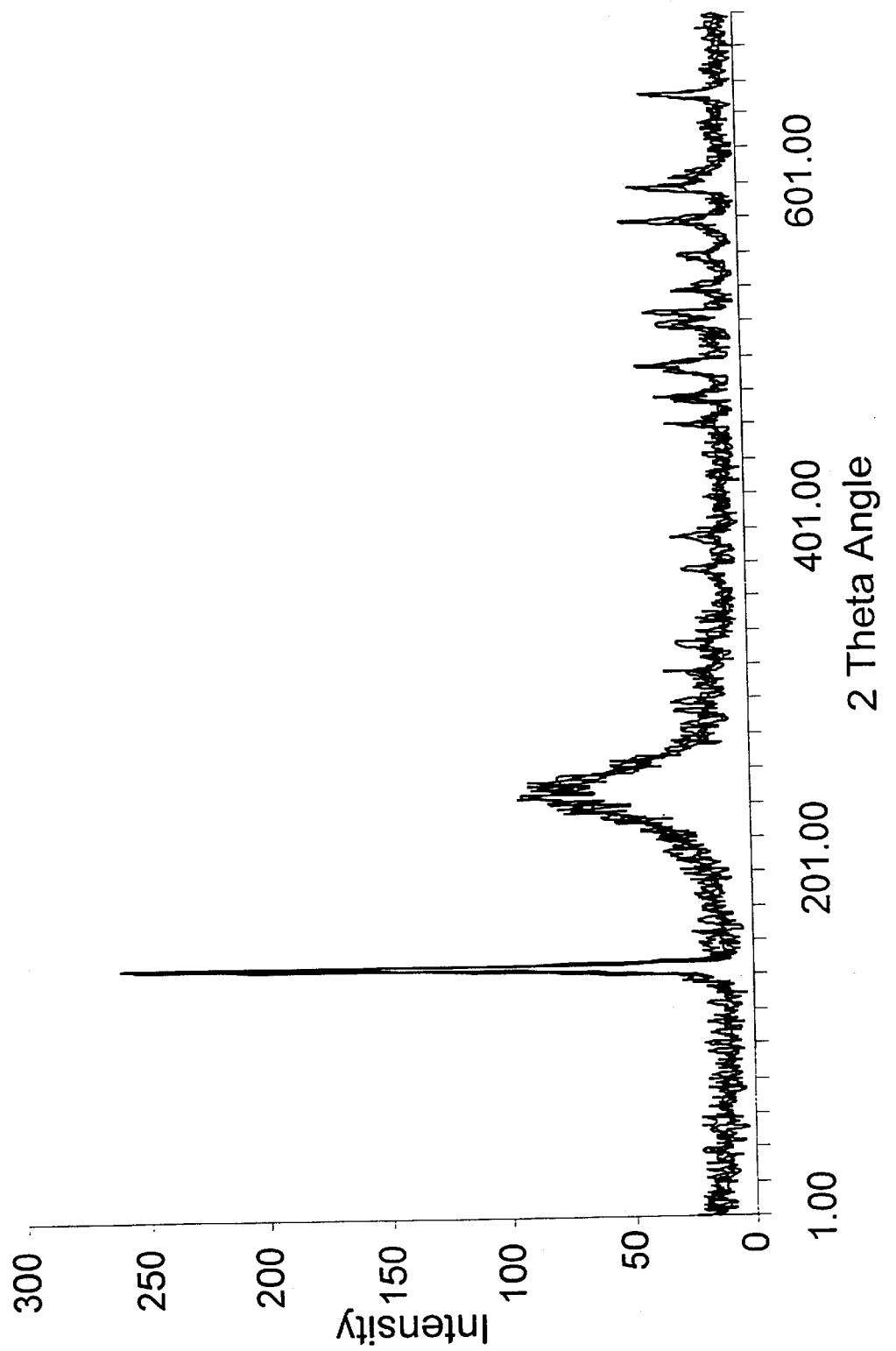
FIG. 17 is overlaid X-ray powder diffraction patterns corresponding to cluster $C_2$ of FIG. 15.
Figure 18:
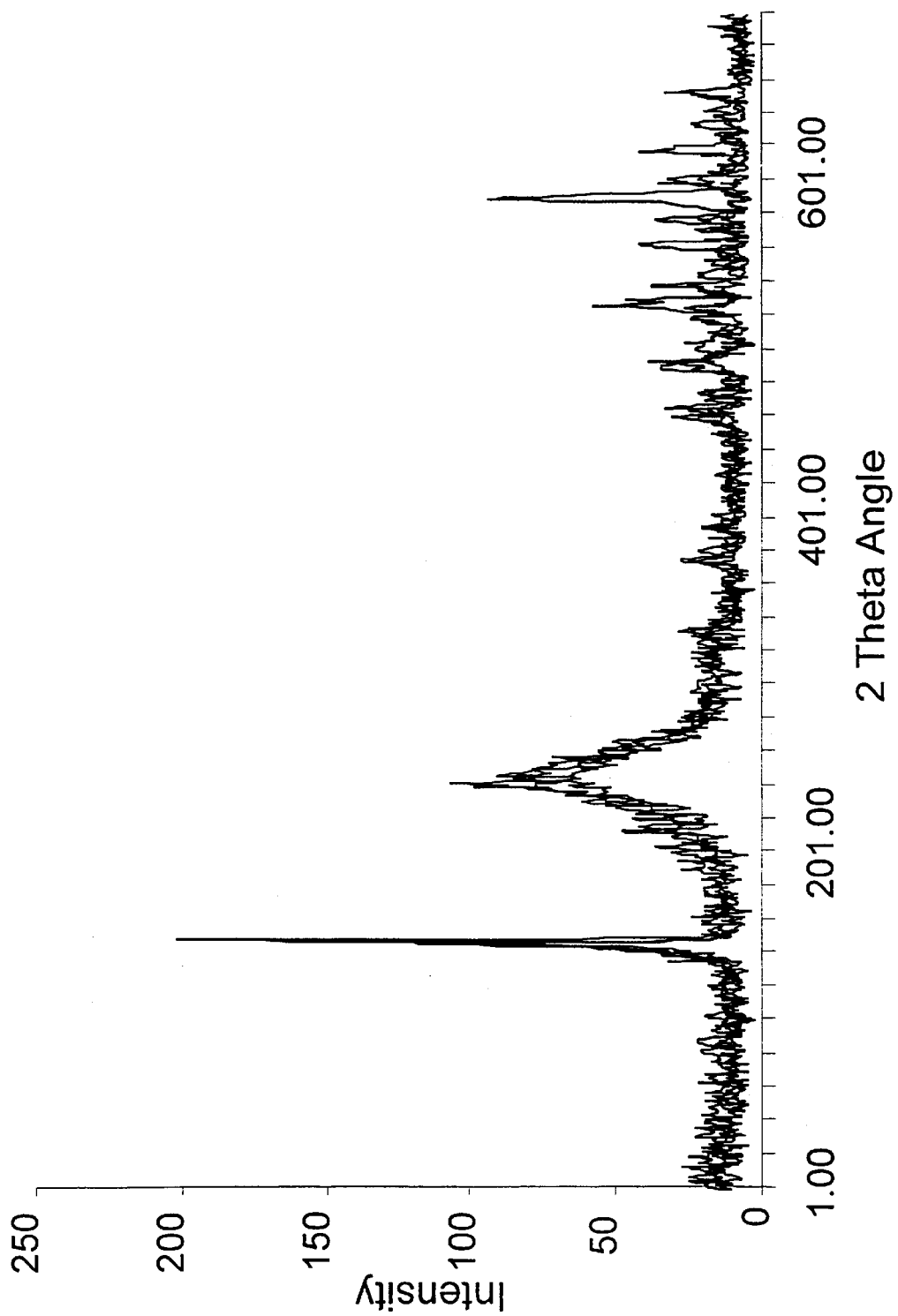
FIG. 18 is overlaid X-ray powder diffraction patterns corresponding to cluster $C_3$ of FIG. 15.
Figure 19:
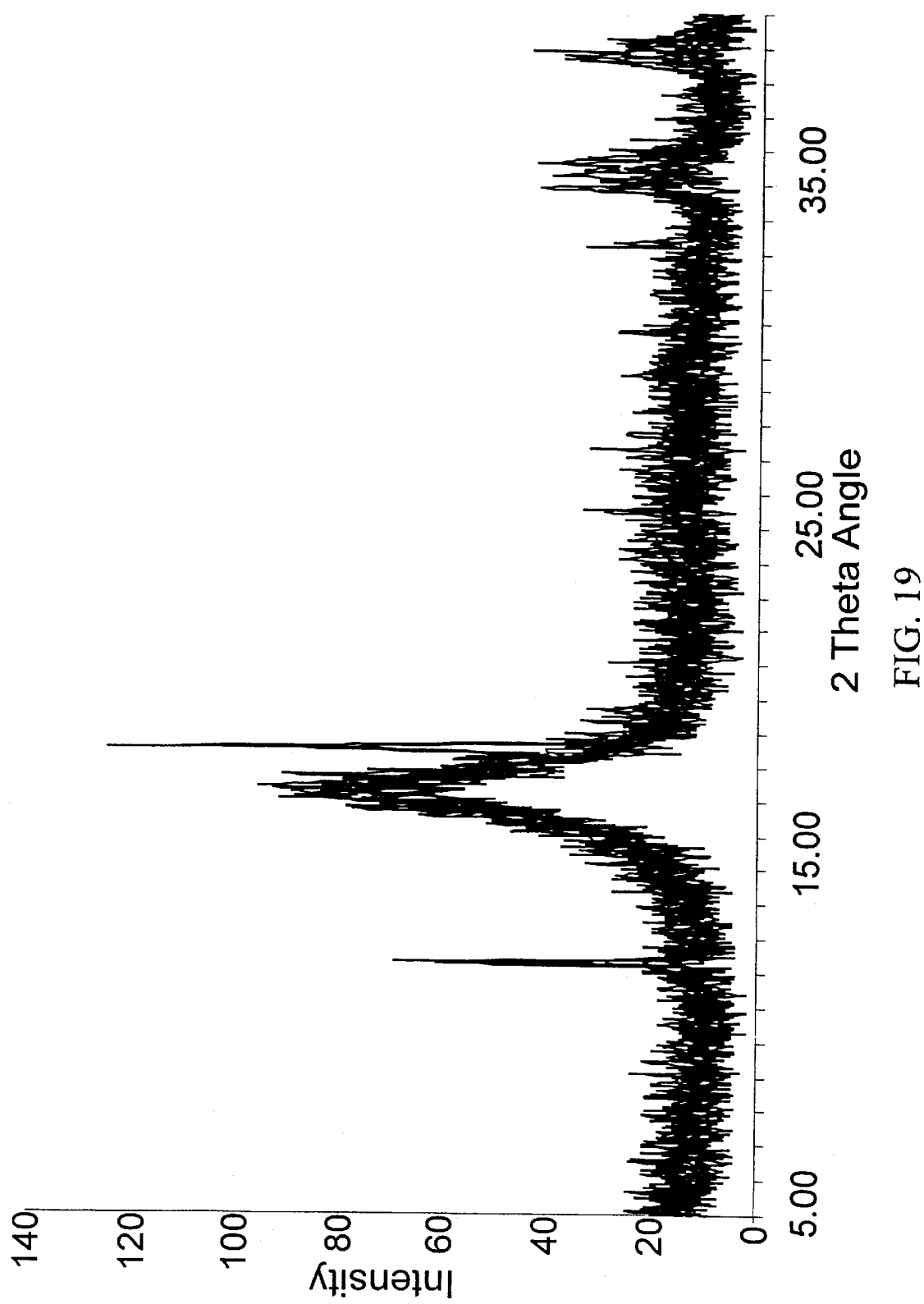
FIG. 19 is overlaid X-ray powder diffraction patterns corresponding to cluster D of FIG. 11.

These two groups of outliers were then removed from the original set of patterns to be analyzed and principal component analysis was performed on the remaining samples to investigate the differences among the members of the main cluster. The resulting plot of the scores is shown in FIG. 11. Visual inspection of the plot shows four main clusters labeled A, B, C, and D. The members of cluster A were identified as a new material designated CuZnVO#12. The overlaid patterns of the members of cluster A are shown in FIG. 12. Cluster B was dominated by a material designated as CuZnVO#6, which was also seen in several of the materials discussed above containing only zinc cations, i.e., no copper. Some of the samples of cluster B contained an impurity designated as ZnVO#1. The overlaid patterns of the members of cluster B are shown in FIG. 13. The cluster labeled C is dominated by the presence of a material designated as CuVO#1 in each of the patterns. The overlaid patterns associated with cluster C.are shown in FIG. 14. Within this cluster can be seen three possible sub-clusters, which have been designated $C_1$, $C_2$, and $C_3$. The X-ray powder diffraction patterns for the samples in cluster C were analyzed by principal component analysis and the resulting plot of the scores are presented in FIG. 15, where the three sub-clusters became apparent. FIG. 16 shows the X-ray powder diffraction patterns associated with cluster $C_1$, which correspond to the CuVO#1 structure plus a peak at 3.02 Å. FIG. 17 shows the X-ray powder diffraction patterns associated with cluster $C_2$ and demonstrates that the members of the $C_2$ cluster contained only CuVO#1. FIG. 18 shows the X-ray powder diffraction patterns associated with cluster $C_3$ and demonstrates that cluster $C_3$ contained CuVO#1 and a few peaks from minor components. The fourth cluster, labeled D, contained samples that did not have much crystalline material as evidenced by the noise level in the patterns, shown in FIG. 19. The peaks at high angle correspond to CuO. The remaining scores on the plot of FIG. 11 do not cluster well, which indicated that they were unique from one another and should be analyzed individually, one at a time. Among the remaining samples, the members furthest from the origin contained the new material CuZnVO#1.

What is claimed is:

1. A method of screening multiple X-ray powder diffraction patterns corresponding to a set of samples comprising:
    a) determining by principal component analysis a number of factors which can be used in combination with scores of the factors to express each pattern in the sample set;
    b) determining the scores of each factor for each X-ray powder diffraction pattern of the sample set;
    c) plotting the scores in 2- or more dimensional space; and
    d) inspecting the plot of the scores.

2. The method of claim 1 wherein inspecting the plot of the scores results in identifying characteristics selected from the group consisting of outliers, clusters, and trends.

3. The method of claim 2 wherein the inspecting is performed visually.

4. The method of claim 2 further comprising determining the structure of one sample in a cluster from the corresponding X-ray powder diffraction pattern by comparing to known X-ray powder diffraction patterns.

5. The method of claim 4 further comprising assigning the structure determined for one sample in a cluster to all samples within that cluster.

6. The method of claim 2 further comprising determining one outlier or clustered sample to represent erroneous data from the corresponding X-ray powder diffraction pattern.

7. The method of claim 6 further comprising assigning the erroneous data designation determined for the one sample in a cluster to all samples within that cluster.

8. The method of claim 2 further comprising determining the structure of at least one sample in each cluster from the corresponding X-ray powder diffraction patterns by comparison to known X-ray powder diffraction patterns.

9. The method of claim 8 further comprising assigning the structure determined for one sample in a cluster to all samples within that cluster.

10. The method of claim 2 further comprising determining the structure of at least one outlier by comparing the X-ray powder diffraction pattern of the outlier to known X-ray powder diffraction patterns.

11. The method of claim 2 further comprising identifying the structure of one sample in a cluster as being novel by comparing the X-ray diffraction pattern of the one sample to known X-ray powder diffraction patterns.

12. The method of claim 11 further comprising assigning the novel structure determined for the one sample in a cluster to all samples within that cluster.

13. The method of claim 1 wherein at least one of the samples has a known structure, and identification of unknowns is made by noting clustering about this known sample pattern.

14. The method of claim 1 wherein the number of factors is 2, 3, 4 or 5.

15. The method of claim 2 wherein the inspecting is performed using statistical parameters selected from the group consisting of K-nearest neighbors, Mahalanobis distances, density mapping, Jardine and Sibson's node analysis, Forgy's method of centroids, MASLOC method of centrotypes, fuzzy clustering, Minimum spanning tree method, and McQueen's K-means method to identify the characteristics.

16. The method of claim 2 further comprising:
    a) comparing the X-ray powder diffraction patterns corresponding to the samples in a cluster for differences;
    b) determining by principal component analysis applied to only those X-ray powder diffraction patterns corresponding to the samples in a cluster where the patterns show differences, a number of subset factors which can be used in combination with subset scores of subset factors to express each X-ray powder diffraction pattern in the subset of samples;
    c) determining the subset scores of each subset factor for each X-ray powder diffraction pattern of the subset of samples;
    d) plotting the resulting subset scores in 2- or more dimensional space; and
    e) inspecting the plot of the subset scores.

17. The method of claim 16 further comprising repeating acts (a) through (e) until no differences are observed in the X-ray powder diffraction patterns.

18. The method of claim 1 further comprising:
    a) selecting a subset of samples and their corresponding X-ray powder diffraction patterns;
    b) determining by principal component analysis a number of subset factors which can be used in combination with subset scores of subset factors to express each X-ray powder diffraction pattern in the subset of samples;
    c) determining the subset scores of each subset factor for each X-ray powder diffraction pattern of the subset of samples;
    d) plotting the resulting subset scores in 2- or more dimensional space; and
    e) inspecting the plot of the subset scores.

19. The method of claim 17 where said subset of samples belong to a cluster of claim 2.

20. The method of claim 17 further comprising repeating, at least once, acts (a) through (e) where each iteration uses a selected number of the previous subset of samples.

21. The method of claim 17 wherein the inspecting of the plot of the scores results in identifying characteristics selected from the group consisting of outliers, clusters, and trends.

22. The method of claim 17 further comprising using statistical parameters selected from the group consisting of K-nearest neighbors, Mahalanobis distances, density mapping, Jardine and Sibson's node analysis, Forgy's method of centroids, MASLOC method of centrotypes, fuzzy clustering, Minimum spanning tree method, and McQueen's K-means method to identify clusters, trends, and outliers.

* * * * *